United States Patent

Lindh

[11] Patent Number: 5,571,210
[45] Date of Patent: Nov. 5, 1996

[54] ADJUSTABLE FOOT PROSTHESIS

[75] Inventor: Leif Lindh, Danderyd, Sweden

[73] Assignee: Pro-Pel AB, Danderyd, Sweden

[21] Appl. No.: 347,331

[22] PCT Filed: Jun. 2, 1993

[86] PCT No.: PCT/SE93/00492

§ 371 Date: Dec. 2, 1994

§ 102(e) Date: Dec. 2, 1994

[87] PCT Pub. No.: WO93/24080

PCT Pub. Date: Dec. 9, 1993

[30]  Foreign Application Priority Data

Jun. 2, 1992 [SE] Sweden ............................. 9201720-1

[51] Int. Cl.⁶ .................................................. A61F 2/62
[52] U.S. Cl. ................................ 623/38; 623/53
[58] Field of Search ................................ 623/38, 55, 53, 623/47, 50, 52, 35, 59

[56]  References Cited

U.S. PATENT DOCUMENTS

| 292,800 | 2/1884 | Furrer | 623/53 X |
| 1,294,632 | 2/1919 | Dickson | 623/38 X |
| 4,446,580 | 5/1984 | Furuya et al. | |
| 4,865,611 | 9/1989 | Al-Turaiki | |
| 5,458,656 | 10/1995 | Phillips | 623/27 |

FOREIGN PATENT DOCUMENTS

| 0280004 | 8/1988 | European Pat. Off. | 623/53 |
| 0611553 | 7/1926 | France | 623/53 |
| 358818 | 9/1922 | Germany | |
| 2101303 | 6/1972 | Germany | |
| 469780 | 9/1993 | Sweden | |
| 9100070 | 1/1991 | WIPO | 623/53 |

OTHER PUBLICATIONS

Lehmann et al., "Trends in Lower Extremity Bracing", Archives of Physical Medicine & Rehabilitation, Jun. 1970, p. 350.

*Primary Examiner*—David H. Willse
*Attorney, Agent, or Firm*—Kane, Dalsimer, Sullivan, Kurucz, Levy, Eisele and Richard, LLP

[57]  ABSTRACT

A foot prosthesis has a support part and a foot element which cooperates with the support part. The foot element includes a forefoot part which is displaceable axially along the support part. The foot element further includes a heel part which is fixed on the lower end of the support part. A setting arrangement sets the position of the forefoot part along the support part in relation to the heel part.

14 Claims, 6 Drawing Sheets

ADJUSTABLE FOOT PROSTHESIS

The invention relates to a foot prosthesis comprising a support part and a foot element cooperating with the support part.

Foot prostheses of different types are known. Prostheses are usually designed in such a way that an ordinary shoe can be used on top of the prosthesis. At a defined heel height, for which the setting has been made upon production of the individually adapted prosthesis, the prosthesis is considered easy to walk on and to load, but without a shoe, or at another heel height, the prosthesis is no longer comfortable to use, since the angle of the foot in relation to the ground surface is no longer correct.

The most common solutions to the above problem are either to angle the whole foot prosthesis downwards/forwards or to lower the heel part when, for example, it is desired to walk without a shoe. Angling the prosthesis downwards does not produce an anatomically correct shaping of the foot, i.e. the type of foot setting which is required when using a higher heel is not obtained, and if, alternatively, the heel section is lowered, this results instead in a lengthening of the leg, which will cause discomfort, particularly in the back.

SE-B-8504225-5 describes a foot prosthesis having a central part, which supports the sole, heel and leg part. In this prosthesis the heel is movably arranged in relation to the central part of the prosthesis and to that part of the sole of the foot which is joined in a fixed manner to the central part. Movement of the heel is obtained by virtue of the fact that the latter is coupled together with the rear area of the central part by means of a bar which can be locked in a hole in the said area and is joined to the heel, which bar, in the unlocked position, can be displaced in relation to the central part for the purpose of setting the heel in relation to the sole of the foot. In this arrangement the lengthening of the leg results from the fact that the heel is lowered in relation to a reference point, for example the knee of the user.

WO 91/15171 describes a foot prosthesis having a foot plate and a hollow cylindrical body, which is angled in relation to the foot plate and secured thereon in such a way that mutual relative movement is permitted. The foot also comprises a support which is displaceably and adjustably arranged in the upper part of the cylindrical body and secured on the foot plate at the lower end of the body in such a way that a relative movement can take place between the support and the foot plate. In this case too adjustment of the prosthesis results in lengthening of the leg/shortening of the leg.

U.S. Pat. No. 4,547,913 describes a completely different solution to the problem. Here the prosthesis is made up of three rigidly connected parts—leg part, foot part and heel part—made of fibre-reinforced resin, the material and shaping of the parts giving flexibility to the prosthesis.

EP-A-0444883 additionally indicates a method for solving the problem by connecting a foot part to a tibia part by means of a ball joint.

When producing foot prostheses and leg prostheses, a number of factors have to be taken into account. The normal foot can move in all planes, individually or in combination. The lower leg in a person consists of two bones which, by cooperating with one another and with the ankle joint, permit a rotational movement or torsion of the lower leg, which continues in a rotation of the foot, and in addition the calf muscles of the lower leg provide a pushing-off force which can be varied, i.e. adapted suitable for the specific purpose.

There are at the present time technical solutions for solving this problem to some extent, for example in SE-B-8201389-7 where the foot prosthesis consists of a continuous hollow core which is secured directly on the leg prosthesis adapter piece and which, by virtue of its design with rigid and elastic areas, provides mobility in the dorsal-plantar direction. However, the foot does not have any capacity for energy absorption, it has no adjustable heel, and it is made from heavy, not light, composite material.

Moreover, in the natural foot an adjustment in the attitude of the heel takes place as height of the heel increases. This can be illustrated most clearly by observing the movement which takes place when the foot is to be brought down into a shoe or when walking on tiptoe. What happens is that muscles on the back of the lower leg are contracted and the heel is in this way lifted, but at the same time as the heel is lifted an angling of the forefoot takes place in the care of normal walking movement. The higher the heel is lifted, the greater is the angle obtained between the forefoot and the adjoining part of the foot.

One way of attempting to solve this problem is shown, for example, in the abovementioned SE-B-8504225-5. As has been mentioned above, however, this solution produces a lengthening of the leg, and a problem therefore arises if it is assumed that the prosthesis user only requires a prosthesis on one foot.

In addition, as has been mentioned above, there are prostheses on the market where the user can alter the height of the heel above the walking surface, for example by using a spanner for manual adjustment of the height of the heel, but none of these alter the characteristics of the foot, but only the angle of the foot in relation to the leg.

Further prostheses, which constitute the state of the art, are described, for example, in U.S. Pat. No. 4,306,320, U.S. Pat. No. 4,364,128, U.S. Pat. No. 4,413,360, U.S. Pat. No. 4,636,220, U.S. Pat. No. 4,446,580 and DE-C-358818. However, it should be noted that no energy-absorbing foot exists whose setting can be varied by the user.

An object of the invention is to avoid the abovementioned problems of the known foot prostheses, and in this way to provide a prosthesis which is at all times comfortable for the user, regardless of the height of the heel, and which can satisfy the varying requirements of the prosthesis user for force in the kicking-off moment.

The aim of the present invention is to provide a prosthesis of the type mentioned in the introduction, in which a setting of the prosthesis for different heel heights and kicking-off force (energy absorption) is achieved, so that an essentially physiologically correct functioning is obtained. By virtue of the fact that the material in the prosthesis parts additionally has an energy-absorbing function, a variable pushing-off force is obtained (see above description regarding the normal foot and muscles of the lower leg).

A further aim is to provide an energy absorption which can be varied in a simple manner with regard to the requirements of the prosthesis user at a given moment, for standing, walking or running. When walking, and in particular when running, the force which is required for the kicking-off movement increases. With the prosthetic foot according to the invention this is achieved by virtue of the fact that the front part of the prosthesis is displaced in the distal direction, as a result of which a more powerful pushing-off force is obtained upon unwinding of the step, which is required when the user wishes to run.

A further aim is to facilitate walking uphill and downhill. Normally, the walking foot angles to the extent necessary for obtaining the pushing-off force which is needed. This too is achieved as a result of the design of the prosthesis according to the invention, by virtue of the fact that the prosthesis user can quickly and easily adjust the setting of the foot part in the vertical direction by means of a simple hand grip.

A further aim is to be able to adjust the prosthesis for walking on different types of ground surface. The pushing-off requirement varies greatly depending on the characteristics of the ground surface, such as, for example, grass or sand or a firm surface. This problem is also solved with the aid of setting the prosthesis.

These aims are achieved according to the invention by virtue of the fact that the foot element comprises a forefoot part which is arranged in such a way that it can be displaced in the axial direction along the support part, a heel part which is fixed on the lower end of the support part, and a setting arrangement for setting the vertical position of the forefoot part in relation to the heel part.

A further aim is that it will be possible for this setting of the prosthesis to be carried out simply and by the prosthesis user himself or herself, without the prosthesis having to be removed. In principle, it will be possible for this alteration to be made using a single hand grip.

These aims are achieved according to the invention by virtue of the fact that the setting arrangement comprises operating mechanisms for altering the displacement of the forefoot part along the support part, stops for limiting the displacement of the forefoot part along the support part, and also retention means for holding the forefoot part in the set position.

According to an embodiment of the invention, this is achieved by means of operating mechanisms being arranged to displace the forefoot part slidably along the support part. Within the scope of the invention, these mechanisms can be designed in various ways. For example, a wire can be arranged running from an attachment device which is placed at a suitable position in the vicinity of or on the prosthesis socket and which can be controllably adjusted, and running to that area of the forefoot part which constitutes its attachment element round the support part, the attachment element and with it the forefoot part being spring-loaded by means of a spring mechanism for the purpose of holding the forefoot part in the set position. In the event of the functioning of the attachment elements failing, this spring mechanism also acts to return the forefoot to a position defined by a stop which has been arranged either on the support part or on a guide part provided. More details regarding this guide part are given below.

This described adjustment of the setting of the forefoot part in the vertical direction in relation to the heel part can of course be obtained by means other than have been described here. The adjustment can for example be carried out steplessly or in stages, it being possible for this to be achieved by using, as described below, a wire for transmission of movement. Another way can be to arrange force-transmitting and movement-transmitting mechanisms inside the support part, which consists of a tube at whose lower end the forefoot part is secured, and to adjust the vertical setting via these mechanisms.

According to an embodiment of the invention, the adjustment can also be obtained by virtue of the fact that the forefoot part and the heel part are joined in a mutually displaceable manner by means of a threaded rod which joins the two parts and which, in combination with force-transmitting means, produces a desired displacement of the forefoot part along the support part.

This displacement can be achieved by virtue of the fact that a setting arrangement is provided on one of the attachments of the foot element on the support part and is actively connected to the said rod in order to effect the displacement of the forefoot part along the support part.

A further aim is that it will be possible to adapt the prosthesis to the individual who is to use it, and that this will be made possible by combining, in a suitable manner, different heel and forefoot parts having different physical properties. The prosthetic foot should therefore be easy to secure, set and adjust in the desired manner.

This is achieved by virtue of the fact that the prosthesis according to the invention is made up of a forefoot part and a heel part, which parts can be designed in such way that respective parts have properties differing from each other, i.e. a forefoot part can be combined with different heel parts having different characteristics, and vice versa. These parts can thus be combined with each other as required, taking into consideration the weight of the prosthesis user, the required activity etc. in each individual case. The material which is used for these parts should be a so-called energy-absorbing material, such as composites of various types, for example carbon fibre, glass fibre, etc. By designing the forefoot part with an attachment element round the support part, an intermediate part and a foot plate part, the foot is given flexibility. The movement capacity of the prosthesis can additionally be increased, for example by dividing the foot plate part, in a manner known per se, into several parts by arranging at least one slot in the foot plate part, which slot divides the foot plate into two parallel parts in its length and in this way permits a further possibility of flexibility in the prosthesis.

A further aim is to provide a certain torsional capacity in the prosthesis so that it is comfortable to use and of a physiologically correct design.

As has been pointed out above, the lower leg has two bones which cooperate with one another and which, upon rotation of the foot, are displaced in relation to one another. This rotational movement also occurs when walking and needs to be compensated in the prosthesis. If no torsion is permitted in the case of a prosthesis user when walking, that part of the leg which is nearest the socket will absorb all the torsional movement, which is caused by the torsional forces arising during the walking movements.

In order to produce the abovementioned compensation in the prosthesis according to the invention, a guide part is arranged essentially parallel to the longitudinal direction of the support part. These two parts, the support and guide part, together constitute an assembly which solves this problem by virtue of the fact that, on the one hand, they are joined via the attachment element of the forefoot part round the support part, where the guide part runs through the same attachment element, and, on the other hand, by virtue of the fact that the guide part, here a guide pin, is fixed in connection to the lower end of the support part. The support part will in this way function as a shaft around which torsional movement can take place, and the guide part, depending on its material properties, such as bending capacity, rigidity, energy-absorption, will determine the torsion characteristic. In addition to this compensation, a further compensation takes place in the forefoot part upon pushing-off and in the heel part when setting the foot down, as a result of the intrinsic properties of these parts. In the example described below, the guide part has been positioned behind the support part, but this is not necessary, and satisfactory functioning can also be obtained if the guide part is positioned anywhere around the support part, preferably in front of the support part.

According to a further embodiment of the invention, this can be achieved by virtue of the fact that the guide part, which is joined between the attachment element of the heel part connected in a fixed manner to the support part and the displaceable attachment element of the forefoot part, provides a possibility of torsional movement between the said attachment elements.

According to the invention it is also possible to adjust the setting of the heel in a simple manner, so that its tread surface assumes a suitably adapted angle with respect to the ground surface, which angle gives the underside of the heel part a position essentially parallel to the ground surface.

This can be achieved by virtue of the fact that elements are provided for adjusting the angle of the contact surface of the heel part in relation to the ground surface and the support part, and also for adjusting the rigidity of the heel part.

Preferred embodiments of the invention have been given the features cited in the subclaims.

By means of the foot construction, in which the mobility and setting possibilities, both upon production of the prosthesis and later upon use thereof, are to a large extent based on the fact that a prosthesis is formed round the standard tube which is normally used for securing prosthetic feet on and that there is a possibility of torsion round the said tube, a high degree of mobility of the foot is achieved, and at the same time the use of energy-absorbing material gives it an additional flexibility.

The invention is described in greater detail below with reference to the attached drawings, which show preferred embodiments.

Figure 1:
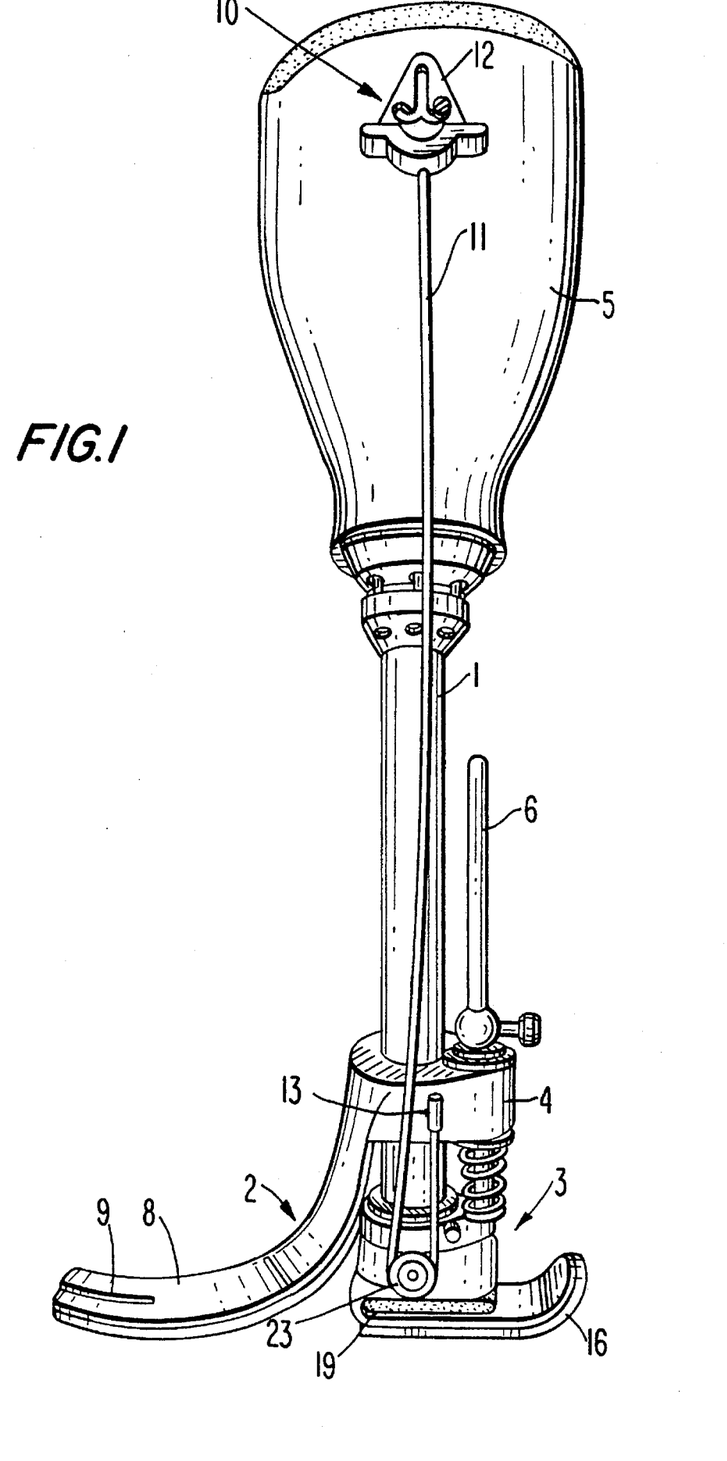
FIG. 1 shows an embodiment of the foot prosthesis according to the invention fitted on a prosthesis socket with tube.

FIG. 1 shows a prosthesis according to the invention, which has a prosthesis socket 5, a tube 1 below called support and a foot part. This tube is preferably an ordinary standard tube of the type which is commonly used for securing prosthetic feet on prosthesis sockets and which in this case constitutes a replacement of the lower leg, either completely or partially. A forefoot part 2 is arranged in a displaceable manner on this tube, referred to hereunder as the support part 1, and a heel part 3 is arranged in a fixed manner on the lower end of the support part 1. The figure also shows a setting arrangement, generally designated by 10, for setting the vertical position of the forefoot in relation to the lower end of the support part, i.e. in relation to the heel part. This arrangement consists of a wire 11 whose lower end is arranged in a fixed manner at an attachment point 13 on the attachment element 4 of the forefoot part, which attachment element 4 surrounds the support part 1, and whose other end is arranged at a variable attachment element 12 on the prosthesis socket 5. Between these attachment points the wire runs via a roller 23 positioned on the heel part 3 fixed to the support part 1. By regulating the setting of the variable attachment element 12, the forefoot part 2 can be raised and lowered in relation to the heel part 3, i.e. displaced along the support part 1. In addition to those parts of the prosthesis which have already been described, a guide part 6 is also included in the form of a rod which is arranged essentially parallel to the tube 1 and which gives a possibility of torsion in the joint, but which prevents rotation of the forefoot part round the support part. This guide part 6 has a further role, namely to give a possibility of torsion in the prosthesis, which will be discussed in greater detail below. In FIG. 1 it is also shown that the forefoot part 2 can have a slot 9 in the direction of the foot plate 8, as viewed from the front edge, in which case the forefoot part including the foot plate 8 should be made of a material with suitable flexibility in order to simulate the function of the natural foot.

As a result of the material and design of the forefoot part, its attachment element round the support part 1 will pinch firmly and strengthen the grip round the tube upon loading.

Figure 2A:
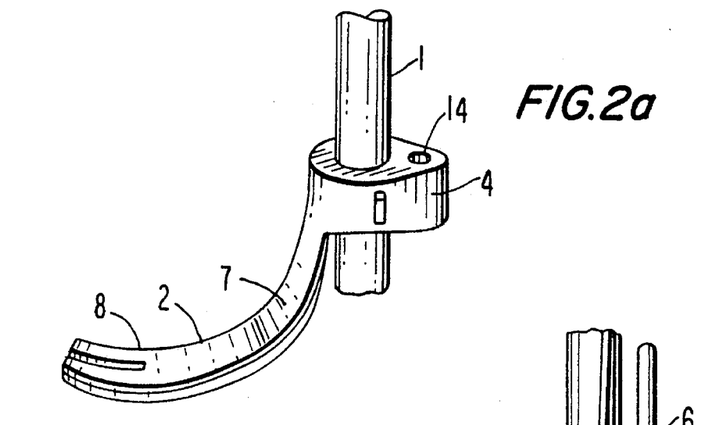
FIGS. 2a and b show both parts (forefoot part and heel part) of the foot prosthesis individually.
Figure 2B:
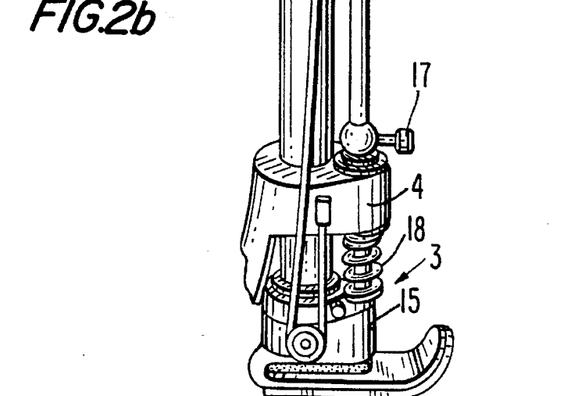

FIGS. 2a and b show the foot prosthesis in greater detail. The construction of the forefoot part 2 is shown in FIG. 2a. The part comprises an annular part 4, referred to above as the attachment element of the forefoot part, intended to be arranged displaceably on the support part 1, an intermediate part 7 and a foot plate 8. The annular part 4 has, on the side opposite the foot plate, a through-hole 14 for receiving a guide part 6, not shown in a displaceable manner. FIG. 2b shows how this guide part 6 is arranged in a fixed manner on the lower part of the support part, more precisely on the attachment element 15 of the heel part 3. A return spring 18 is arranged round the guide part 6 between the attachment element 15 of the heel part 3 and the attachment element 4 of the forefoot part. On the guide part 6 above the attachment element 4 of the forefoot part a stop 17 is arranged as a safety means which, in the event of a possible failure of any of the parts of the control arrangement, comes into operation and prevents the displacement of the forefoot upwards along the support part any further than the position which corresponds to the positioning of the heel and forefoot in relation to each other when the heel height is lowest. This in order to ensure that the foot prosthesis can still be used in the event of the above occurring.

In this connection it should be pointed out that the control arrangement described above and shown in FIGS. 1 and 2b does not necessarily have to be designed in accordance with the figure, but instead the wire 11 can, for example, run directly from its lower attachment element to the upper attachment element without passing any type of pulley or roller. However, in this case the return spring 18, which is mentioned above, should be displaced to a position above the attachment element of the forefoot part round the guide part 6 or round the support part 1 and under the stop 17, which is shown in FIG. 4.

It should be mentioned here that the positioning of the guide part 6, as shown in the figures, is not the only one possible, but in order to achieve a desired torsional capacity in the prosthesis the guide part should be positioned essentially parallel to the support part and preferably right behind or right in front of the latter, as viewed in the longitudinal direction of the prosthetic foot.

Figure 3:
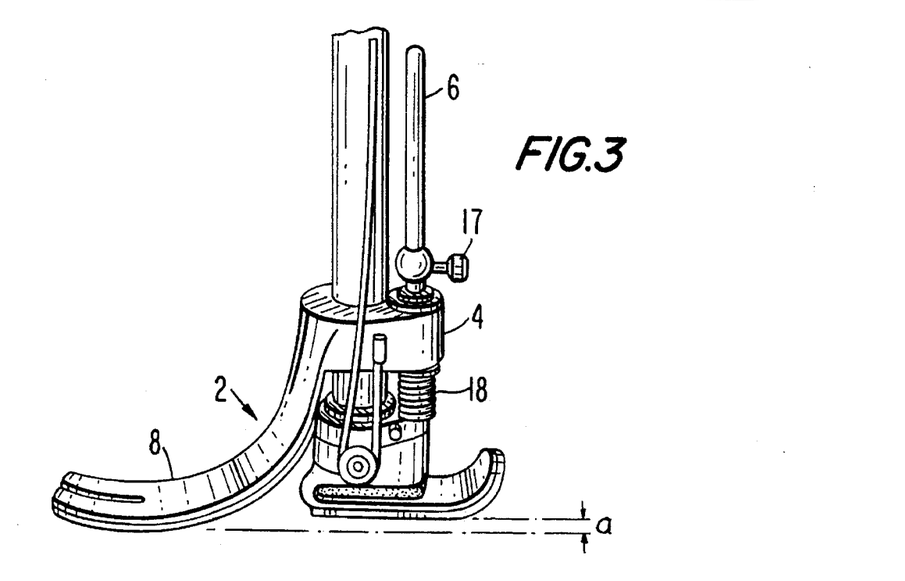
FIG. 3 shows the prosthesis in the position set for a higher heel height.

FIG. 3 shows how the appearance of the prosthesis is changed when the forefoot part is lowered, in order to permit a higher heel height. In this position the spring 18 thus assumes a compressed state. The distance a shown corresponds to the displacement of the forefoot part along the support part and corresponds to the desired heel height. The reference numerals given in FIG. 3 correspond to the numbers in FIG. 2a and 2b.

Figure 4:
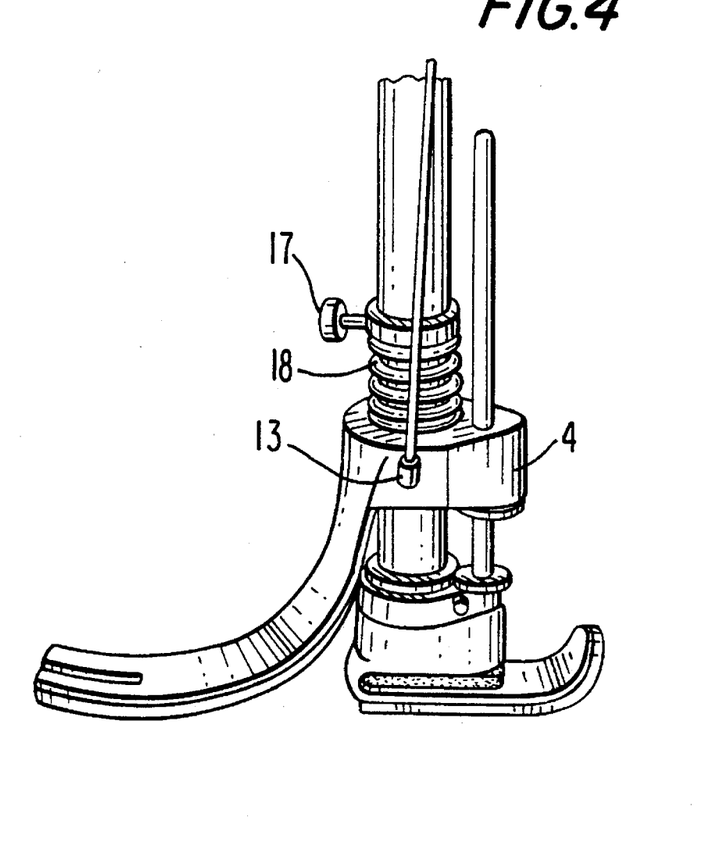
FIG. 4 shows an alternative embodiment of the prosthetic foot.

FIG. 4 shows the positioning of the return spring round the support part 1 above the attachment element 4 of the forefoot part, which attachment element 4 surrounds the support part when the wire runs directly from the attachment element 13 on the forefoot part to the variable attachment element 12 on the prosthesis socket 5 not shown. The spring shown here is not in its most compressed position, but is compressed to such an extent in relation to its strength that it suitably balances the force in the wire.

Figure 5:
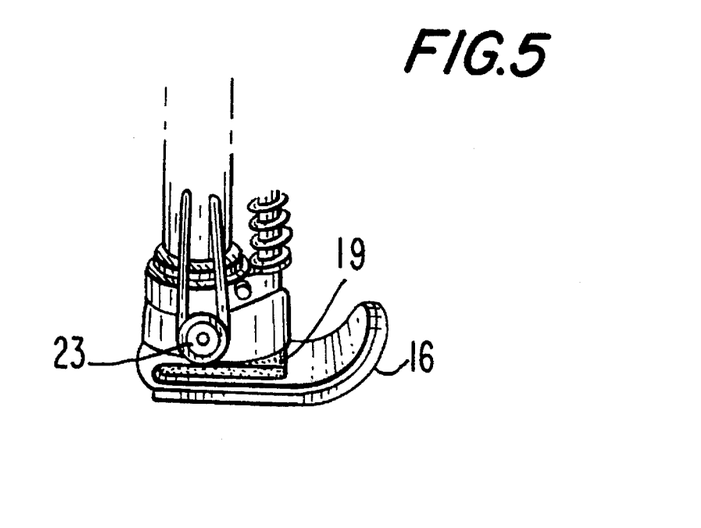
FIG. 5 shows a detailed view of the heel part as seen from the side.

FIG. 5 shows a detailed view of the heel part as seen from the side. The heel part consists of a plate 16 which constitutes the supporting surface via which the prosthesis upon use rests in contact with the ground surface, and on which the greatest part of the load is exerted, since the plate 16 is situated essentially under the support part 1. This plate 16 is made of a suitable material with specially adapted hardness and flexibility in order to constitute, on the one hand, a stable standing surface and in order to be resilient, on the other hand, in the rear part of the heel so as to permit in this way a natural setting down of the heel on the ground surface. Arranged between this plate 16 and the support part is an insert 19, which can be adapted individually taking into consideration the weight of the prosthesis user, the activities, etc. This insert can, as in this case, be in the form of a plate of uniform height. It can also be wedge-shaped, and it can be designed in such a way that it can be changed or replaced by the actual prosthesis user.

In a further embodiment according to the invention, this insert or element 19 can be replaced by exchangeable rollers of varying diameter and hardness intended to be inserted and replaced via the outer cosmetic shell of the prosthesis or to be stationary and of an expanding type in such a way that they can be acted upon, using a tool provided for this purpose, so that their diameter is altered.

Figure 6:
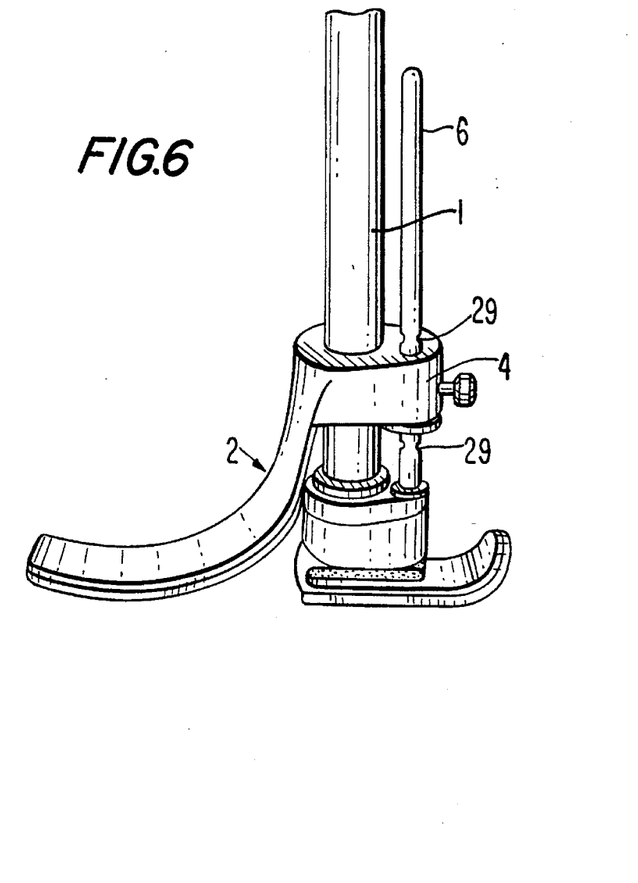
FIG. 6 shows an alternative embodiment of the setting arrangement of the forefoot part.

FIG. 6 shows an alternative embodiment of the invention in which the displaceably arranged attachment part 4 of the forefoot part 2 has a nut (not shown) which is set into the rear side and through which a threaded pin can be screwed in order to lock the forefoot part securely in the desired vertical position with regard to the support part 1. This is achieved by virtue of the fact that the guide part 6 is provided with through-holes 29 in which the pin is inserted in such a way that the forefoot part is locked securely at the desired height. Here too some type of stop can of course be arranged as a safety means. The pin mentioned here can also be a spring-loaded pin which is brought in the same way toward the holes in the guide part and which snaps into position upon adjustment. In both these cases the pin is arranged in such a way that, when the forefoot part is in the locked position, the head of the pin bears against the nut (not shown).

An additional possible solution is obtained if the guide part 6, instead of being arranged in a fixed manner on the lower end of the support part, is arranged in a fixed manner on another part of the support part, parallel to the latter and with the attachment point above the attachment element of the forefoot. By proceeding in this way a cooperation corresponding to that which has already been described is obtained between the support part, the forefoot part and the guide part.

Figure 7:
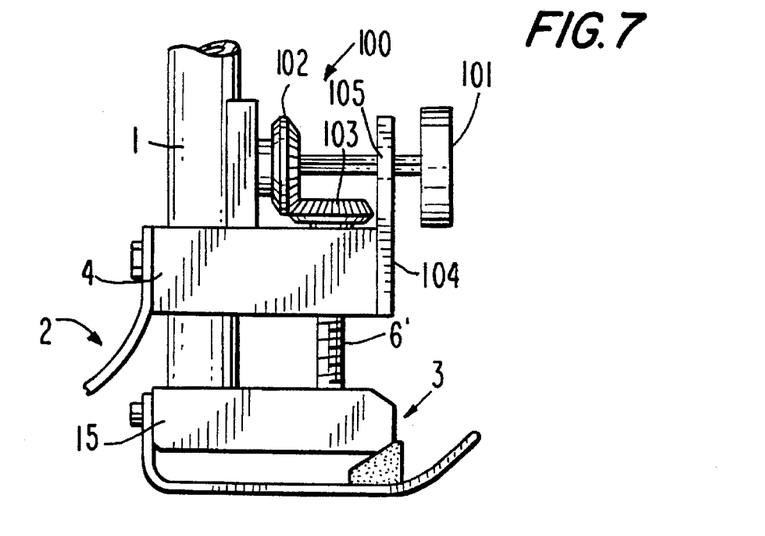
FIG. 7 shows a further setting arrangement in side view.

FIG. 7 shows a further alternative embodiment of the invention, in which the setting arrangement 100 for setting the vertical position of the forefoot part 2 in relation to the heel part 3 comprises a guide part 6 which is arranged between the attachment element 15 of the heel part arranged in a fixed manner on the support part 1 and the displaceable attachment element 4 of the forefoot part round the support part 1, which guide part in this case consists of a threaded rod 6' which can be elastically secured in the attachment element 15 of the heel part 3 for the purpose of adjusting the vertical position of the forefoot in relation to the heel part 3. The elastic securing is intended to provide a certain possibility of torsion in the prosthetic foot. The threaded rod 6' passes through an essentially vertical hole through the rear part of the attachment element 4 of the forefoot part, and the upper end of the rod continues through the center of a mounted conical, horizontal gear wheel 103 (driven) arranged on the rear part of the topside of the forefoot part 2, which actively cooperates with the threaded rod 6'. This gear wheel is in turn driven by a mounted conical, vertically arranged gear wheel 102 (driving) in whose center a recess (not shown) is arranged for a hexagon spanner 101. Arranged parallel to and at a distance from this gear wheel is a bracket 104 in which a through-hole 105 is positioned in line with the abovementioned hole in the center of the gear wheel 102. This hole 105 is intended for guiding the abovementioned hexagon spanner. By turning the gear wheel 102 round, the forefoot part 2 is made to move along the rod 6' and thus along the support part by means of cooperation with the gear wheel 103.

A stop for the upward movement of the forefoot part can consist of the bracket 104 and, for the downward movement, of the attachment element 15 of the heel part.

In this embodiment the retention means can consist, for example, of the fact that the pitch of the threaded rod is self-locking or that a predetermined friction is produced between, for example, the attachment element 4 of the forefoot part and the gear wheel 103.

Figure 8:
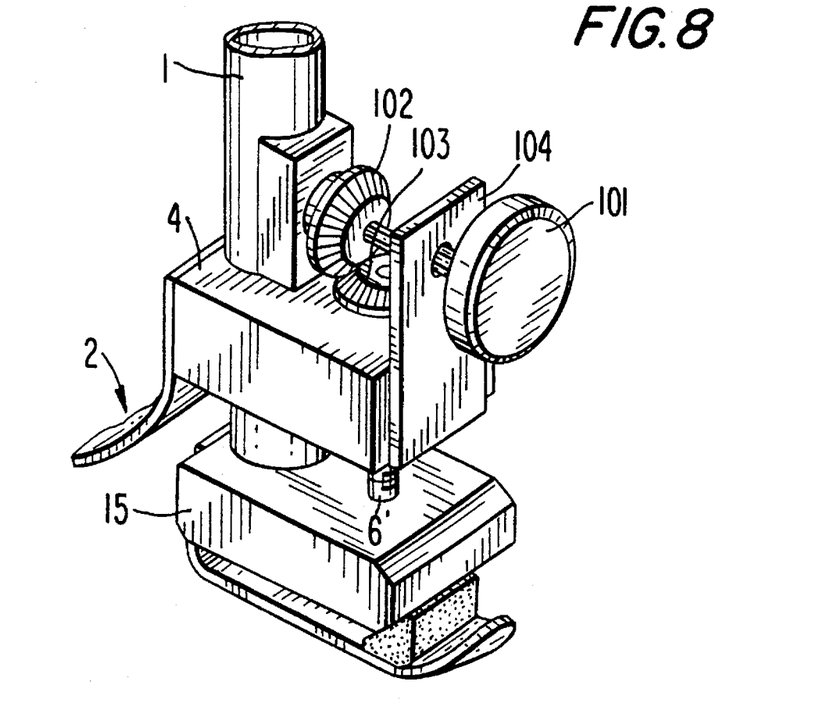
FIG. 8 shows the setting arrangement according to FIG. 7 obliquely from behind.
Figure 9:
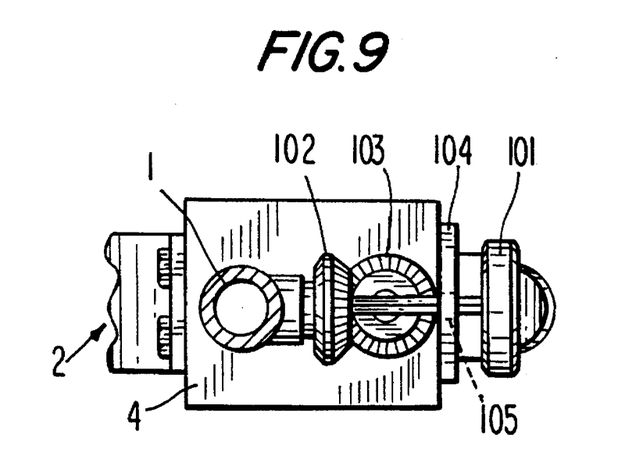
FIG. 9 shows the setting arrangement according to FIG. 7 from above.

FIGS. 8 and 9 illustrate the same embodiment seen, on the one hand, obliquely from behind and, on the other hand, from above. The same reference numerals are used in these figures as in FIG. 7.

Figure 10:
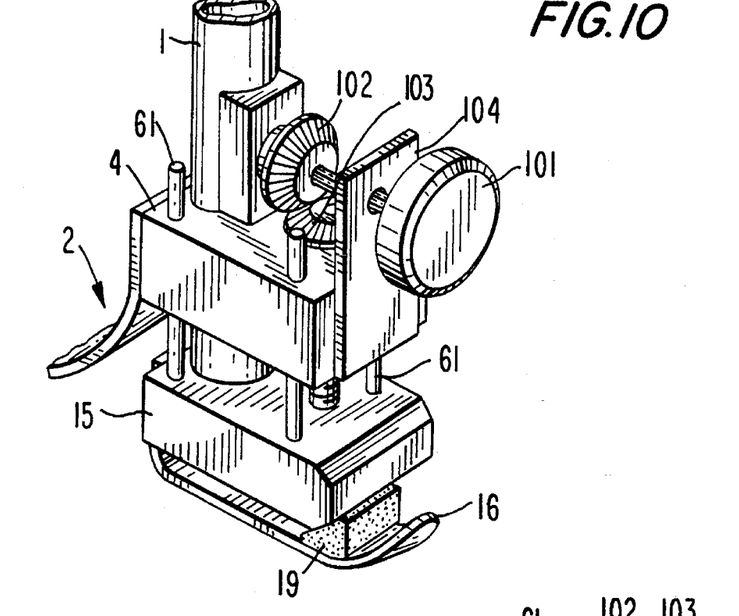
FIG. 10 shows a setting arrangement similar to that in FIG. 7 obliquely from behind.
Figure 11:
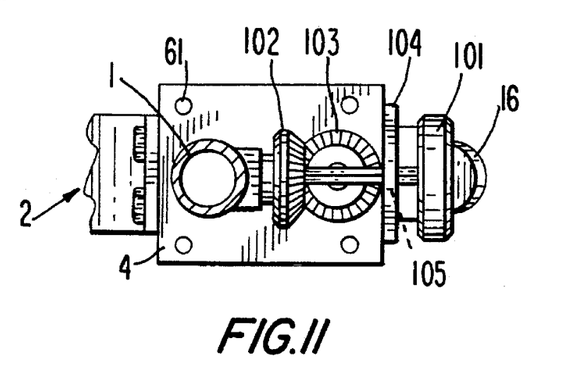
FIG. 11 shows the setting arrangement in FIG. 10 from above.

FIGS. 10 and 11 show a similar embodiment in which four telescopically acting rods 61 for guiding the forefoot part are arranged on the heel part 3. In this case it is not necessary for the annular attachment element of the forefoot part to surround the support part 1 tightly. In this embodiment the number of telescopically acting rods can of course be chosen depending on requirements and objectives. In other respects this embodiment corresponds essentially to that which has been described in FIGS. 7, 8 and 9. The reference numerals in the FIGS. 10 and 11 correspond to the ones in FIGS. 7, 8 and 9.

Figure 12:
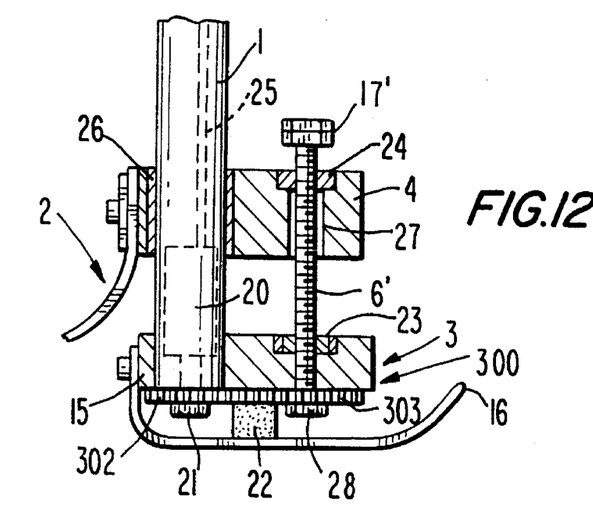
FIG. 12 shows a further setting arrangement in side view, in partial cross-section.

FIG. 12 shows a further embodiment. In this embodiment the setting arrangement 300 for setting the vertical position of the forefoot in relation to the heel part comprises a remote-control motor 20 which, in the present case, is fitted in the support part 1. Running from this motor through the tube 1 is a mains cable 25 for current supply and control of the motor. A slide bushing 26 is arranged between the support part and the attachment element 4 of the forefoot part. In addition, the setting arrangement comprises an essentially vertically arranged hole 27 in the rear part of the attachment element 4 of the displaceable forefoot part round the support part 1. Arranged in this hole is a nut 24 or the like, which can be elastically mounted.

Movement of the nut is permitted preferably in a direction transverse to the longitudinal direction of the prosthetic foot in order, in this way, to provide a possibility of a certain torsion in the prosthesis. The guide part is passed through the nut 24 and the hole 27, this guide part in this case consisting of a threaded rod 6' which cooperates with the nut 24. The lower end of this rod passes through a corresponding through-hole, provided with a bushing and a guide bearing 23, in the rear end of the attachment element 15 of the heel part, and is connected in a fixed manner, on the underside of the said attachment element 15, to a driven gear wheel 303 by means of a securing arrangement 28, the gear wheel 303 being driven in turn by a driving gear wheel 302, functionally connected via a shaft 21 to the remote-controlled motor 20.

When the motor, which is incorporated here in the support part, is operated by a remote control, the forefoot part will move up or down along the support part as a result of the cooperation between the rod 6' and the elastically mounted nut arranged on the rear part of the annular attachment element 4 of the forefoot part round the support part 1.

A stop 17' for the upward movement of the forefoot part can consist of two nuts drawn towards one another.

Even in this embodiment the retention means can consist of self-locking characteristics in the construction and the motor.

The part 22 consists of two identical parts, of which only the further is visible, and which are arranged between the plate 16, constituting the contact of the heel part with the walking surface, and which correspond to the inserts 19 which can be seen, for example, in FIG. 1.

In these last two main types of embodiment, the movement which is produced in the forefoot part by means of the gear wheels 102, 103 and 302, 303, respectively, should be obtained by arranging a ball screw at a suitable position for cooperation with the threaded rod 6.

The invention is not limited to the embodiments described above and shown in the drawings, but can be modified within the scope of the patent claims attached.

I claim:

1. An adjustable foot prosthesis comprising a prosthesis socket; an elongated support part securing a foot element to said prosthesis socket; said foot element cooperating with said support part, said foot element comprising a forefoot part, having a forefoot attachment element slidably disposed on said support part, said forefoot part thereby being slidingly displaceable in an axial direction along said support part, and a heel part, said heel part being fixed on an end of said support part opposite to said prosthesis socket; and a means for setting the position of said forefoot part on said support part.

2. An adjustable foot prosthesis as claimed in claim 1 further comprising a guide part, said guide part being a rod extending from said heel part parallel to said support part and through said forefoot attachment element toward said prosthesis socket, and wherein said forefoot attachment element is slidably disposed on said guide part.

3. An adjustable foot prosthesis as claimed in claim 2 wherein said means for setting the position of said forefoot part on said support part comprises:

a spring disposed about said guide part between said heel part and said forefoot attachment element;

a stop element affixed to said guide part and separated thereon from said spring by said forefoot attachment element;

a variable attachment element on said prosthesis socket;

a roller on said heel part;

an attachment on said forefoot part; and a wire, said wire running from said variable attachment element, around said roller, and to said attachment on said forefoot part.

4. An adjustable foot prosthesis as claimed in claim 2 wherein said means for setting the position of said forefoot part on said support part comprises:

a spring disposed about said support part between said prosthesis socket and said forefoot attachment element;

a stop element affixed to said support part between said spring and said prosthesis socket;

a variable attachment element on said prosthesis socket;

an attachment on said forefoot part; and a wire, said wire running from said variable attachment element to said attachment on said forefoot part.

5. An adjustable foot prosthesis as claimed in claim 2 wherein said guide part has a plurality of holes, said holes being arranged at intervals longitudinally therealong, and wherein said means for setting the position of said forefoot part on said support part comprises a threaded pin threadingly secured in said forefoot attachment element and protrudable into one of said plurality of holes.

6. An adjustable foot prosthesis as claimed in claim 1 further comprising a guide part, said guide part being a threaded rod extending from said heel part parallel to said support part and through said forefoot attachment element, said guide part being threadingly engaged in said heel part, and wherein said means for setting the position of said forefoot part on said support part comprises a first conical gear attached to said guide part at said forefoot attachment element, and a second conical gear mounted on said forefoot attachment element.

7. An adjustable foot prosthesis as claimed in claim 6 wherein said second conical gear has a central recess by which it may be rotated with an appropriate tool.

8. An adjustable foot prosthesis as claimed in claim 7 wherein said central recess has the shape of a hexagon.

9. An adjustable foot prosthesis as claimed in claim 8 further comprising a hexagon spanner, said hexagon spanner being said appropriate tool.

10. An adjustable foot prosthesis as claimed in claim 6 further comprising a plurality of telescopically acting guide rods connecting said forefoot attachment element to said heel part.

11. An adjustable foot prosthesis as claimed in claim 1 further comprising a guide part, said guide part being a threaded rod extending from said heel part parallel to said support part and through said forefoot attachment element, said guide part being threadingly engaged in said forefoot attachment element, and wherein said means for setting the position of said forefoot part on said support part comprises a first gear wheel attached to said guide part at said heel part, an electric motor, and a second gear wheel driven by said electric motor, said second gear wheel in turn driving said first gear wheel to change the position of said forefoot part.

12. An adjustable foot prosthesis as claimed in claim 11 wherein said electric motor is disposed within said support part.

13. An adjustable foot prosthesis as claimed in claim 11 wherein said electric motor is a remote-controlled motor.

14. An adjustable foot prosthesis as claimed in claim 11 wherein said heel part comprises a heel plate and an insert between said support part and said heel plate, said insert determining the angle and spacing between the heel plate and the support part.

* * * * *